United States Patent [19]

Griffith et al.

[11] 4,326,037

[45] Apr. 20, 1982

[54] ENZYMATIC METHOD FOR IMPROVING THE INJECTABILITY OF POLYSACCHARIDES

[75] Inventors: William L. Griffith, Oak Ridge; Alicia L. Compere, Knoxville; James W. Holleman, Oak Ridge, all of Tenn.

[73] Assignee: The United States of America as represented by the United States Department of Energy, Washington, D.C.

[21] Appl. No.: 90,176

[22] Filed: Nov. 1, 1979

[51] Int. Cl.³ ............................................. C13L 3/00
[52] U.S. Cl. .................................... 435/274; 166/246
[58] Field of Search ....................... 435/274, 275, 276; 166/246

[56] References Cited

U.S. PATENT DOCUMENTS 3,966,618  6/1976  Colegrove ..................... 166/246 X
4,010,071  3/1977  Colegrove ..................... 435/274 X
4,119,491  10/1978 Wellington ........................ 435/274
4,165,257  8/1979  Stokke .............................. 166/246 X

*Primary Examiner*—Robert J. Warden
*Attorney, Agent, or Firm*—Allen H. Uzzell; Stephen D. Hamel; Richard G. Besha

[57] ABSTRACT

A method for enhancing the ability of polysaccharides in aqueous solution to flow through a porous medium comprises contacting the polysaccharides with an endo-enzyme capable of hydrolyzing at least one of the linkages of the sugar units of the polysaccharides and maintaining the polysaccharides in contact with the enzyme under hydrolysis conditions for a time sufficient to decrease the tendency of the polysaccharides to plug the porous medium yet insufficient to decrease the viscosity of the aqueous polysaccharides by more than 25%. The partially hydrolyzed polysaccharides are useful as thickening agents for flooding water used to recover oil from oil-containing subterranean formations.

9 Claims, 2 Drawing Figures

ENZYMATIC METHOD FOR IMPROVING THE INJECTABILITY OF POLYSACCHARIDES

This invention is a result of a contract with the U.S. Department of Energy.

BACKGROUND OF THE INVENTION

1. Field of the Invention

This invention relates to the preparation of polysaccharides having improved flow properties for use in enhanced oil recovery techniques.

2. Description of the Prior Art

In describing the work of others herein we do not admit that such work is actually prior art under 35 USC 102 or 35 USC 103 or that the work was prior in time to the making of the invention described and claimed herein. We reserve the right to establish a date of conception or reduction to practice prior to the effective date of any publication, patent, or work herein described.

Within recent years polysaccharides have been proposed for use in enhanced oil recovery processes. In micellar flooding techniques, for example, a high viscosity aqueous polysaccharide solution containing surfactants, co-surfactants, or coagents is injected under pressure through an injection well into an oil-bearing formation. The injected fluid flows toward one or more production wells carrying with it or pushing before it a portion of previously unrecovered crude oil. Polysaccharides function as thickening agents in the injected solution to provide high viscosity to control the mobility of the injected fluid through the porous formation. Polysaccharides decrease "fingering" of the flow (the preferential higher velocity flow along wider, more permeable pathways) so that the injected fluid contacts a large portion of the petroleum in place, conducting it toward the production well. Fingering is a major problem, particularly in formations which are interspersed with microscopic cracks and in which pores holding oil are in the 0.1–10 micron range. In such formations it is important that the injected fluid flow through the small pores without plugging while still having sufficient viscosity to flow slowly through large cracks in the strata. Polysaccharides which have been proposed for use in enhanced oil recovery include xanthan gum, scleroglucan, and polyglucosylglucan.

A number of techniques for chemically treating polysaccharides have been reported. For the most part these treatments have been aimed at purification or clarification. For example, in U.S. Pat. No. 3,316,241 Leder et al. describe a process for recovering xanthan gum from its fermentation medium which involves the dispersion of the gum in an organic solvent. Cationic treatment to purify biopolymers from solution has been reported by several workers. See for example McNeeley et al., U.S. Pat. No. 3,232,929; O'Connell, U.S. Pat. No. 3,355,477; and Patton et al., U.S. Pat. No. 3,382,229. Treatment with alkali metal salts is described in Buchanan et al., U.S. Pat. No. 3,773,752. Quaternary amine precipitation for purifying polysaccharides is described in Rogovin et al, U.S. Pat. No. 3,119,812 and Gill et al., U.S. Pat. No. 3,422,085. Lindblom et al. in U.S. Pat. No. 3,163,602 describe a method of preparing substituted heteropolysaccharides involving the reaction of fermenter broth with quaternary ammonium compounds. In U.S. Pat. No. 3,729,460 Patton describes the alkaline treatment of a heteropolysaccharide for clarification. The clarification was thought to be due to deacetylation and also some degree of depolymerization.

Enzyme treatments to decrease the plugging tendencies of polysaccharides have recently been reported by Colegrove in U.S. Pat. No. 4,010,071 and Wellington in U.S. Pat. No. 4,119,491. Colegrove and Wellington each describes a protease enzyme treatment for enzymes of microbiological origin. The protease enzymes were said to specifically attack cell-wall fragments suspended in solution, thereby reducing the tendency of these fragments to plug porous formations.

OBJECTS OF THE INVENTION

It is an object of this invention to provide an enzyme treatment method for modifying polysaccharides to improve their ability in aqueous solution to flow through porous media.

It is a further object to provide such an enzyme treatment which does not substantially reduce the viscosity of aqueous solutions of the polysaccharides.

It is a further object to provide a method of recovering oil from an underground formation using the enzymatically treated polysaccharides.

SUMMARY OF THE INVENTION

This invention is a controlled enzymatic hydrolysis method for enhancing the ability of a polysaccharide in an aqueous solution to flow through a porous medium which the aqueous polysaccharide has a tendency to plug. The method of this invention comprises contacting the polysaccharide with an endoenzyme capable of hydrolyzing at least one of the linkages between sugar units of the polysaccharide and maintaining the polysaccharide in contact with the enzyme under hydrolysis conditions for a time sufficient to decrease the tendency of the polysaccharide in aqueous solution to plug the porous medium, said time insufficient to decrease the viscosity of said aqueous polysaccharide solution by more than 25%. It has been demonstrated that endoenzyme hydrolysis can increase the flux of a polysaccharide solution by 50% or more. Based upon known sugar linkages in the polysaccharide structure, suitable endoenzymes can be selected from standard classification references and from information usually supplied with commercial enzyme products. Alternatively, endoenzymes capable of the desired controlled hydrolysis can be found empirically by separating readily available commercial enzyme mixtures and screening the separated fractions. This screening can be performed by treating the subject polysaccharide, or a polysaccharide having at least some common linkages between sugar units with the separated fractions and experimentally determining which fractions are capable of decreasing the plugging tendencies while not reducing the viscosity excessively. In its oil-recovery aspects, this invention is a method for recovering oil from an oil-containing subterranean formation penetrated by an injection means and a production means which comprises injecting through said injection means and into said formation flooding water containing as a thickening agent a polysaccharide treated according to the above endoenzyme hydrolysis.

DETAILED DESCRIPTION OF THE INVENTION

Figure 1:
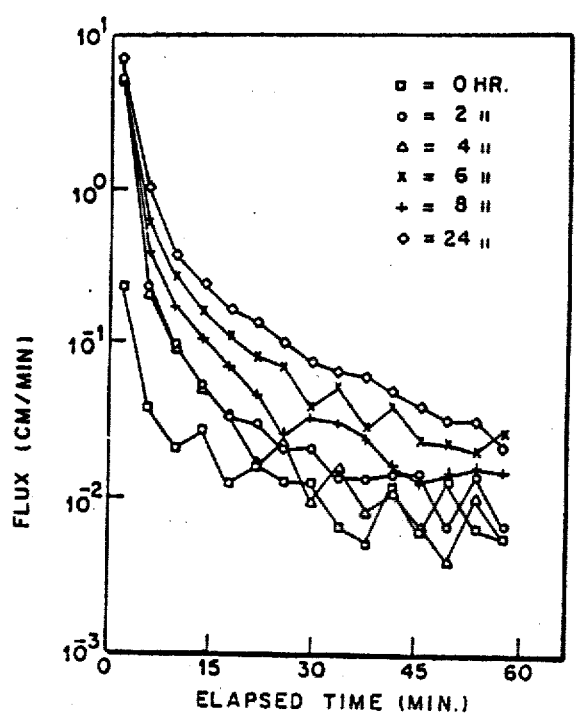

An aspect of this invention is the discovery that polysaccharides, when treated with endoenzymes capable of hydrolysis of at least one of the linkages between sugar units, have a decreased tendency in aqueous solution to plug a porous formation through which the solution is passed. For purposes of this invention, the ability of a solution to flow through a porous medium is the flow velocity or volumetric flow rate obtained when a constant fluid pressure difference occurs across the porous medium. The tendency of the solution to plug a porous medium is defined as the decrease in the volumetric flow rate or velocity (i.e., flux) of the solution through the medium with passing time, while the temperature and the pressure difference across the medium are held constant. An example of a model porous medium for which the plugging tendencies can be reduced is one having a majority of the pore volume present as pores having diameters (equivalent sphere diameter) in the range of 0.1-10 micrometers.

Endoenzymes, useful according to this invention, are enzymes which are capable of making midchain breaks in the polysaccharide chain, that is, breaks at positions other than the end sugar units. Such enzymes are en-dopolysaccharide hydrolases. While we do not wish to be bound by any theory, it is believed that enzymes which preferentially attack the central portions of the polymer chain reduce the amount of polymer aggregates in aqueous solution by reducing the intertwining among polymer molecules, thereby reducing the plugging tendencies of the solution. The action of endoenzymes is contrasted to that of exoenzymes which attack the end linkages of the polysaccharides and produce only a minimal change in the solution properties. The action of exoenzymes can be readily distinguished from the action of the endoenzymes of this invention because exoenzyme hydrolysis causes the release of monosaccharide reducing sugars.

The hydrolysis with endoenzymes according to this invention is quite distinct from chemical hydrolysis of polysaccharides. Chemical hydrolysis is a random attack, which greatly decreases the viscosity of polysaccharide solution and would seriously affect its utility as a thickening agent in oil recovery. Endoenzyme hydrolysis being selective for midchain linkages between sugar units can greatly reduce the plugging tendency of solutions with only minor reductions in solution viscosity. In some cases the reduction in polymer aggregates by partial endoenzyme hydrolysis can also enhance the optical clarity of the solution. Consequently, it is contemplated that the endoenzyme treatment of this invention will be useful for clarifying gums and polysaccharides used in food products and cosmetics.

Endoenzymes which are useful for reducing the plugging tendencies of polysaccharides may hydrolyze the polysaccharide to the extent that desirable physical properties are lost. The enzyme treatment of this invention should therefore be controlled so that the viscosity of an aqueous solution of the polymer after treatment is at least about 75% of the viscosity of the solution of the same concentration prior to enzyme hydrolysis. The measurement of the solution viscosity is a convenient method for monitoring the progress of the hydrolysis, which can then be terminated before the viscosity is decreased to an unacceptable level.

Polysaccharides which are contemplated as suitable for enzyme treatment according to this invention include the biogums, including gums from plant sources such as guar gums, cellulose gums, acacia gums, locust bean gum, starches, and okra gum, as well as microbial gums such as dextrins, dextrans, mannans, xanthans (e.g. produced by the genus Xanthomonas), scleroglucans, and algal gums.

Enzymes suitable for modification of polysaccharides according to this invention are those of the class of polysaccharide hydrolase endoenzymes which are capable of attacking at least one midchain linkage in the main polymer chain. For example, scleroglucan having a main chain of poly-beta-1,3-glucosylglucose is attacked midchain by an endo-beta-1,3-glucosyl-glucanohydrolase. A different polymer with a repeating unit of beta-1,4-mannosyl-, beta-1,3-glucosyl-, beta-1,2-glucosylglucose could be treated by the enzymes endo-beta-1,4-mannosylglucanohydrolase, endo-beta-1,3-glucosylglucanohydrolase, or endo-beta-1,2-glucosyl-glucanohydrolase. All that is necessary to perform the controlled enzymatic hydrolysis of this invention is to contact the polysaccharide with a suitable endoenzyme or mixture of suitable endoenzymes and to maintain the polysaccharide in contact with the enzyme or enzymes under hydrolysis conditions for a time sufficient to obtain the desired reduction in plugging tendencies yet insufficient to reduce the viscosity of the polysaccharide in solution to less than above 75% of its original viscosity.

The controlled endoenzyme hydrolysis of this invention can be performed by any of the well-known methods of enzyme treatment. The preferred method of carrying out the hydrolysis is to pass the polysaccharide in an aqueous solution through a column having the endoenzymes attached to a particulate support material such as Raschig rings, ceramic articles such as alumina beads or pellets, glass beads, cross-linked polymeric supports, or other non-reactive supports. The bound enzyme column is operated under normal hydrolysis conditions of pH, temperature, etc., as are well known in the art. The column can be easily regulated by adjusting the flow rate, etc., to control the residence time of the polysaccharides so as to prevent excessive reduction in viscosity, i.e., greater than 25% reduction. It is preferred that the viscosity of the hydrolyzed polymer in aqueous solution be at least 90% of the viscosity of an aqueous solution of the same concentration of untreated polymer. Preferably the enzyme treatment is carried out for sufficient time to increase the flux (i.e., velocity) of the polysaccharide in solution through a porous medium by at least 50% relative to the flux of an untreated polysaccharide solution of the same concentration passed through the porous medium for the same period of time, up to 1 hour.

The following examples illustrate the enzyme treatment process of this invention.

EXAMPLE 1

Treatment of Scleroglucan

A culture of *Rhizopus arrhizius* Qm 1032, obtained from the U.S. Army Quartermaster Corps, Natick, Mass., was incubated on a BSP medium. *Rhizopus arrhizius* QM 1032 is known in the art to produce an endo-laminarinase, an enzyme which makes midchain breaks between 1-3-beta-linked glucoses comprising luminarin. The BSP medium was prepared by adding 170 g bran, 10 g Soytone (Difco Cat. No. 043601), 10 g Peptone (Difco Cat. No. 0118-01) and 1 g $MgSO_4$, and diluting to one liter with water. The medium was placed to a depth of 1 inch in Fernback Flasks (DiFco Cat. No. 2550-02800) and autoclaved for 1 hour at 121° C. Bran, which has a high concentration of beta-1,3-glucan linkages, was used as a carbon source in order to increase the amount of beta-1,3-glucan hydrolyzing enzyme produced by the incubated cultures. The fungus culture was incubated in contact with the BSP medium at 23°–28° C. on a rocker platform (Bellco Cat. No. 7740-20020, setting No. 5). After the bran paste had been liquefied, the resulting medium/fungal mycelium mixture was diluted 2:3 with water, blenderized, and centrifuged. The centrifuged pellets were washed and resuspended in water and recentrifuged. Pooled supernatants were precipitated with ammonium sulfate at 70% of ammonium sulfate saturation at 18°–19° C. The precipitate was resuspended in distilled water, and desalted by adding 0.6 g of Sephadex G-10 per ml of liquid, followed by a vacuum filtration on a sintered glass funnel after 4 hours at 4° C. The desalted protein (the filtrate) was lyophilized.

The filtrate from 500 ml of *Rhizopus arrhizius* QM 1032 culture was crosslinked onto the surface of one-quarter inch diameter alumina beads by treatment with glutaraldehyde in the following manner. The lyophilized enzyme was dissolved in water, brought to a volume of 50 ml and poured over 300 ml of one-quarter inch alumina beads. The beads were continuously agitated as the liquid was poured over them. Agitation was continued until the beads appeared dry. To the dry beads was added 100 milliliters of 0.5% aqueous glutaraldehyde. The mixture was tumbled slowly for 1 hour in a Bellco roller bottle (Cat. No. 7730-38260) on a Bellco roller apparatus (7730-7500 series). Another 100 ml of the 0.5% glutaraldehyde solution was added, followed by 1 hour of tumbling. One ml of ethanolamine was added and the beads agitated manually for two minutes. The liquid was poured off and the beads were rinsed with 0.5 M citrate buffer, pH 4.5, containing 0.01 M $MgSO_4$. The coated beads were freeze-dried for storage.

A scleroglucan solution was passed through a vertical column containing the coated beads. The scleroglucan solution contained 0.5% by weight scleroglucan, 0.05 M citric acid buffer, pH 4.5, with 0.01 M $SO_4$ ion. For runs expected to last over about 5 hours, as was generally the case, 0.01% by weight dinitrophenol was added to the scleroglucan solution to prevent substantial bacterial growth. Prior to passage through the column, the scleroglucan solution was autoclaved for one-half hour at 121° C. and when necessary stored in sealed vials under refrigeration.

The scleroglucan solution was treated with the bound enzyme on the coated beads by recirculating the solution through the enzyme column with a slow-speed pump until equilibrium was reached, after 2–3 days. The scleroglucan samples were diluted, 30 ml scleroglucan to 270 ml of deionized water, and passed through the column for residence times ranging from 2 to 24 hours at 50° C. The reducing-sugar content of the enzymatically treated scleroglucan solution was not measurable according to the techniques used, which indicated that no more than a very low level of hydrolysis of end-chain sugar units had occurred.

Plugging tests were performed by passing the partially hydrolyzed scleroglucan through a membrane having a very fine pore size. A pipe reservoir with 400 ml capacity was used having a small membrane filter mounted on a flange below the reservoir. The membrane filter was supported by a porous metal frit, having a filter area of 1.44 $cm^2$ recessed into the flange. The resultant assembly was pressurized to provide enough volume to test flow for a period of 1 hour. The membrane was a 1.2 micrometer Gelman Acropor membrane pressurized under 15 psig. The polymer solution had a concentration of about 500 milligrams of polymer per liter. The dilution water had been filtered through media with a greater retention (about 0.8 micrometer) than that of the Acropor membrane. The viscosity of the treated solution was slightly greater than that of solutions prior to passage through the enzyme column. The flux (fluid velocity) of the polyglucan solutions treated for different times was recorded every four minutes and plotted versus the elapsed time in the plugging test. As shown in FIG. 1, the initial increase in flux was more than an order of magnitude greater than the flux of the untreated scleroglucan polymer. After the polymer had passed through the porous membrane for 30 minutes, the polymer which had been hydrolyzed for 6–24 hours had a flux several times greater than the untreated polymer solution. After 60 minutes the polymers hydrolyzed for 6–24 hours still had at least about 50% greater flux than the untreated polymer.

It will not always be necessary, according to this invention, to obtain purified enzymes. Commercially available crude enzyme mixtures can be fractionated, for example, by ammonium sulfate precipitation, and the fractions can be tested to determine empirically which enzymes or enzyme mixtures are effective for increasing the ability of the polysaccharide solution to flow through a porous medium of the desired size range without decreasing the viscosity to less than 75% of its untreated value. Such a screening is illustrated in Example 2.

EXAMPLE 2

Figure 2:
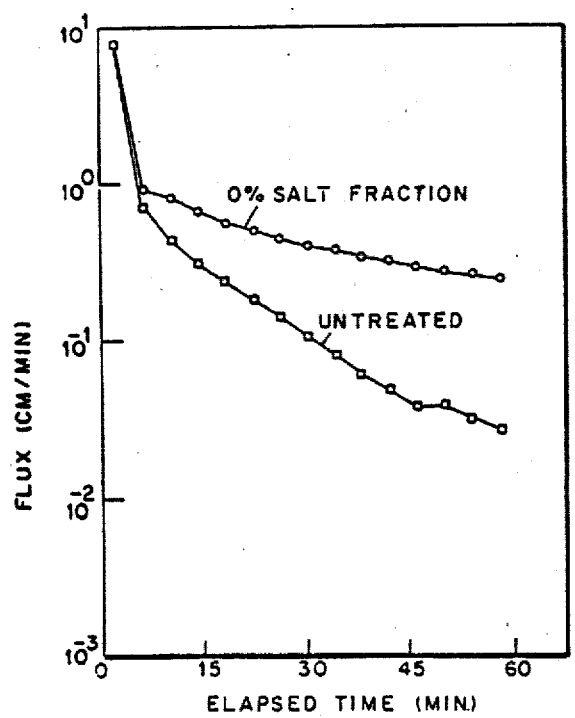

Rohm and Haas HP-150 is a food-grade enzyme product which is marketed for decreasing the viscosity of vegetable gums, i.e., polysaccharides. Ten grams of dried HP-150 enzyme concentrate was diluted to 100 milliliters volume in 0.05 M citrate buffer containing dissolved magnesium. Undissolved material was removed at this point and designated the 0% cut. Additional cuts were taken by adding ammonium sulfate at 5% saturation intervals and removing precipitated material, up to 70% saturation. Each cut was used to hydrolyze a xanthan gum solution. The xanthan polysaccharide was a fine dry powder obtained as Kelco Xanfld, batch XFL-14630. The powder was suspended in 100 milliliters of 0.5 M sodium citrate buffer (containing 0.1 M $MgSO_4$) and 400 milliliters of distilled water in a Waring blender by blending 3 minutes at low speed and 3 minutes at high speed. The volume was adjusted to about 1 liter and the pH was adjusted to 4.5. The suspension was placed in serum vials, capped and autoclaved at 121° C. for 30 minutes. One hundred milliliter solutions of 5 grams per liter xanthan containing 0.01 M $MgSO_4$ and 0.05 M sodium citrate buffer (pH 4.5) were contacted at 50° C. for 4 hours with 1/10 of the quantity of enzyme precipitated from each cut. The total HP-150 enzyme prior to fractionation was 10 g. The polysaccharide solution treated with each cut was diluted 10 to 1 with distilled water and subjected to plugging tests as in Example 1 using the 1.2 micrometer pore size membrane. The 0% cut, the dark material which did not dissolve in the citrate buffer, caused a significant improvement in the flow of xanthan through the porous membrane and also increased the viscosity of the sample. The 5 and 10% cuts lowered the viscosity of the test solution without showing a significant effect on the flux. The 15% cut decreased the sample viscosity sharply with a relatively small effect on the flux and the 20% cut appeared to leave the sample viscosity relatively unchanged. The 25% cut provided only a slight increase in viscosity. The 30, 35, 40, 45, and 50% cuts showed a decrease in sample viscosity. The 15–50% cuts showed only relatively minor increases in flux. The 55% cut showed a marked improvement in solution flux but a severe decrease in viscosity. The 60, 65 and 70% cuts had a moderate improvement in flux but accompanied by a decrease in viscosity. Consequently, the preferred enzyme cut of HP-150 for use is the 0% cut; that is, the fraction which is insoluble at a concentration of 10% by weight/volume in pH 4.5 citrate buffer. The results of the plugging test using untreated xanthan polymer and the xanthan treated with the 0% cut are shown in FIG. 2. It is seen that the flux of both cuts decreases with time, indicating some plugging tendency. The flux of the partially hydrolyzed polymer solutions was very high initially and decreased much more slowly than the untreated polymer. After 60 minutes of flow time, the polymer solution treated with the 0% enzyme cut had a flux about 10 times that of the untreated polymer solution. It is expected that certain of the enzyme cuts or fractions can be combined for economic reasons and still achieve the objectives of this invention. When unbound enzymes are added directly to the solution, as in this Example, the hydrolysis can be halted by heating the solution to 80°–90° C. for sufficient time, usually 15–30 minutes, to inactivate the enzymes or by adding inhibitors which decrease enzyme activity.

Based upon the teachings herein, those skilled in the art of enzyme hydrolysis of natural materials can screen virtually any enzyme mixture to determine those fractions which can provide the desired effect on a specific polymer, i.e., an increase in flux accompanied by an improvement or a reduction of no more than 25%, preferably no more than 10% in the viscosity of the solution. In those cases where the enzyme is bound to a column and used repeatedly, the cost of the enzyme is not expected to be a significant portion of the cost of the treated polysaccharide. All that is needed to perform the screening test of this invention is to obtain a mixture of enzymes, divide the enzyme mixture into a plurality of enzyme fractions such as by ammonium sulfate precipitation, and contact the desired polysaccharide or another polysaccharide having linkages between sugar units in common with the desired polysaccharide with one or more of the enzyme fractions and observe the effect of the enzyme fractions on the viscosity and the flux of the polysaccharide in aqueous solution through a porous medium having the desired pore size. One or more of the enzyme fractions can then be selected from those fractions that are observed to increase the flux of the aqueous polysaccharide solution while failing to decrease the viscosity of the polysaccharide solution by more than 25%.

The partially hydrolyzed polysaccharides of this invention can be used in oil-recovery operations as replacement for the polymer thickening agents used in the prior art. All that is necessary is that an aqueous solution, i.e., generally about 0.005–5% by weight, preferably about 0.05–1% by weight, of the modified polysaccharide of this invention be injected as flooding water into an oil-containing subterranean formation penetrated by an injection means and a production means. It is contemplated that surfactants such as petroleum sulfonates can be employed in combination with the modified polysaccharide in order to lower the interfacial tension between the aqueous flooding water solution in the in situ oil, as is customary in the art. An example of a commonly used petroleum sulfonate surfactant is "Petronate L," (Witco Chemical Co., Sonneborn Division, 277 Park Ave., New York, N. Y. 10017). More detailed descriptions of enhanced oil-recovery waterflood techniques in which the polysaccharide of this invention is contemplated to be effective are contained in U.S. Pat. No. 3,373,810, issued to Williams et al., Mar. 19, 1968 for "Waterflood Process Employing Thickened Water" and U.S. Pat. No. 3,305,016 issued to Lindblom, et al., Feb. 21, 1967 for "Displacement of Oil from Partially Depleted Reservoirs;" the disclosures of which are incorporated herein by reference.

The foregoing description of this invention has been presented for purposes of illustration and description and is not intended to be exhaustive or to limit the invention to the precise forms disclosed. It was chosen and described in order to best explain the principles of the invention and their practical application to thereby enable others skilled in the art to best utilize the invention in various embodiments and with various modifications as are suited to the particular use contemplated. It is intended that the scope of the invention be defined by the claims appended hereto.

What is claimed is:

1. A method for enhancing the ability of a polysaccharide in an aqueous solution to flow through a porous medium, said aqueous solution having a tendency to plug said porous medium, comprising the steps of:
   (a) contacting said polysaccharide with an endoenzyme capable of hydrolyzing at least one of the linkages between sugar units of said polysaccharide, and
   (b) maintaining said polysaccharide in contact with said endoenzyme under hydrolysis conditions for a time sufficient to decrease said tendency of said polysaccharide in aqueous solution to plug said porous medium, said time insufficient to decrease the viscosity of said aqueous polysaccharide solution by more than 25%.

2. The method of claim 1 wherein said maintaining step is carried out for a time insufficient to decrease the viscosity of said aqueous solution by more than 10%.

3. The method of claim 1 wherein said polysaccharide is scleroglucan and said enzyme is produced by *Rhizopus arrhizius*.

4. The method of claim 1 wherein said maintaining step decreases the tendency of said polysaccharide solution to plug said porous medium sufficiently to increase the flux of said solution through said porous medium after one hour by at least 50% relative to untreated polysaccharide.

5. The method of claim 1 wherein said endoenzyme is selected from the group of endo-beta-1,4-mannosylglucanohydrolase, endo-beta-1,3-glucosylglucanohydrolase, and endo-beta-1,2-glucosylglucanohydrolase.

6. The method of claim 5 in which said polysaccharide has a repeating unit selected from the group of beta-1,3-glucosylglucose, beta-1,4-mannosylglucose, and beta-1,2-glucosylglucose.

7. The method of claim 1 in which said polysaccharide is xanthan gum.

8. The method of claim 1 or 7 in which said endoenzyme is obtained empirically from a mixture of enzymes by (a) dividing said mixture into a plurality of enzyme fractions, (b) contacting said polysaccharide, or a second polysaccharide having linkages between sugar units in common with said polysaccharide, with one or more of said enzyme fractions and observing the effect of said contacting on the viscosity and flux of said polysaccharide in aqueous solution, and (c) selecting one or more of said enzyme fractions from those fractions that increase the flux of said aqueous polysaccharide solution in said contacting step while failing to decrease the viscosity of said aqueous polysaccharide solution more than 25%.

9. A method for recovering oil from an oil-containing subterranean formation penetrated by an injection means and a production means which comprises injecting through said injection means and into said formation flooding water containing as a thickening agent a polysaccharide treated according to the process of claims 1, 3, or 7.

* * * * *